United States Patent
Bunick et al.

(10) Patent No.: US 7,078,053 B2
(45) Date of Patent: Jul. 18, 2006

(54) IBUPROFEN COMPOSITION

(75) Inventors: Frank J. Bunick, Randolph, NJ (US); Feng Lin, Havertown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/635,069

(22) Filed: Aug. 5, 2003

(65) Prior Publication Data

US 2004/0048924 A1 Mar. 11, 2004

Related U.S. Application Data

(60) Division of application No. 09/305,027, filed on May 4, 1999, now Pat. No. 6,627,214, which is a continuation-in-part of application No. 09/002,447, filed on Jan. 2, 1998, now abandoned.

(51) Int. Cl.
*A61K 9/28* (2006.01)
(52) U.S. Cl. ..................................................... 424/441
(58) Field of Classification Search ................. 424/441
See application file for complete search history.

(56) References Cited

U.S. PATENT DOCUMENTS

| | | | |
|---|---|---|---|
| 4,279,926 A | 7/1981 | Bruzzese et al. | |
| 4,336,244 A | 6/1982 | Woznicki et al. | |
| 4,687,662 A | 8/1987 | Schobel | |
| 4,753,801 A | 6/1988 | Oren et al. | |
| 4,762,702 A | 8/1988 | Gergely et al. | |
| 4,808,413 A | 2/1989 | Joshi et al. | |
| 4,832,956 A | 5/1989 | Gergely et al. | |
| 4,835,187 A * | 5/1989 | Reuter et al. | 514/570 |
| 4,851,444 A | 7/1989 | Sunshine et al. | |
| 4,867,985 A | 9/1989 | Heafield et al. | |
| 4,868,214 A | 9/1989 | Sunshine et al. | |
| 4,874,614 A | 10/1989 | Becker | |
| 4,888,177 A | 12/1989 | Gergely et al. | |
| 4,900,558 A | 2/1990 | Barry et al. | |
| 5,043,169 A | 8/1991 | Cherukuri et al. | |
| 5,075,291 A | 12/1991 | DuRoss | |
| 5,175,235 A | 12/1992 | Domb et al. | |
| 5,232,735 A | 8/1993 | Kurtz et al. | |
| 5,240,712 A | 8/1993 | Smith et al. | |
| 5,283,065 A | 2/1994 | Doyon et al. | |
| 5,409,711 A | 4/1995 | Mapelli et al. | |
| 5,424,075 A | 6/1995 | Daher et al. | |
| 5,429,825 A | 7/1995 | Reo et al. | |
| 5,445,827 A | 8/1995 | Fritsch et al. | |
| 5,464,632 A | 11/1995 | Cousin et al. | |
| 5,480,652 A | 1/1996 | Bru-Magntez et al. | |
| 5,501,861 A | 3/1996 | Makino et al. | |
| 5,510,385 A | 4/1996 | Stroppolo et al. | |
| 5,541,227 A * | 7/1996 | Loew et al. | 514/568 |
| 5,560,926 A | 10/1996 | Franz et al. | |
| 5,567,437 A | 10/1996 | Bru-Magniez et al. | |
| 5,576,014 A | 11/1996 | Mizumoto et al. | |
| 5,620,965 A | 4/1997 | Blank | |
| 5,631,296 A | 5/1997 | Birrenbach et al. | |
| 5,637,320 A | 6/1997 | Bourke et al. | |
| 5,646,131 A | 7/1997 | Badwan et al. | |
| 5,780,046 A * | 7/1998 | Humber et al. | 424/440 |
| 5,811,131 A | 9/1998 | Mackles et al. | |

FOREIGN PATENT DOCUMENTS

| | | |
|---|---|---|
| EP | 0 181 564 | 5/1986 |
| EP | 0 351 353 | 7/1990 |
| EP | 0 505 872 A1 | 9/1992 |
| EP | 0 753 296 A2 | 1/1997 |
| JP | HEI 9(1997)-2949 | 1/1997 |
| WO | WO 91/16043 * | 10/1991 |
| WO | WO 92/00731 | 1/1992 |
| WO | WO 92/000731 | 1/1992 |
| WO | WO9702017 | 1/1997 |

* cited by examiner

*Primary Examiner*—Zohreh Fay

(57) ABSTRACT

Fumaric acid is added in amounts sufficient to reduce the burn sensation commonly associated with propionic acid derivatives.

8 Claims, No Drawings

IBUPROFEN COMPOSITION

The present application is a division of Ser. No. 09/304,027, filed May 4, 1999 now U.S. Pat. No. 6,627,214, (hereby incorporated by reference herein) which is a continuation-in-part of Ser. No. 09/002,447 that was filed on Jan. 2, 1998 now abandoned (hereby incorporated by reference herein).

BACKGROUND OF THE INVENTION

The present invention relates to ibuprofen compositions, more specifically to ibuprofen compositions with reduced throat burn characteristics.

Many flavors and sweeteners have been added to medication in order to make them more palatable and to mask the unpleasant taste and aftertaste which is common with many medications. Certain medicinal ingredients, in addition to having an unpleasant taste, create a burning or scratching sensation in the throat when swallowed. Flavors and sweeteners do little to overcome this throat burning sensation. Despite numerous efforts to find an effective means to eliminate this burn, there is a continuing need for a method to effectively eliminate the burning sensation with medications, preferably the burn can be reduced to a level such that a chewable composition can be provided.

Ibuprofen is a well known medication which possesses an unpalatable burning sensation in the mouth and throat after ingestion.

Japanese Patent Application 9 (1997)-2949 assigned to American Home Products attempts to eliminate the unpalatable aftertaste by providing only one enantiomer. The patent application discloses the separation of ibuprofen from its racemic mixture to form an orally administered drug composition which contains only the S(+)-ibuprofen and essentially no R(−)-ibuprofen. While this approach may provide a more palatable form of ibuprofen the separation and isolation of the enantiomers are difficult.

U.S. Pat. No. 5,320,855 discloses a method of masking the taste of ibuprofen by granulating with polyvinylpyrrolidone, sodium starch glycolate and sodium lauryl sulfate and coating the resulting granules with hydroxyethyl cellulose or a mixture of hydroxyethyl cellulose and hydroxypropyl methylcellulose. While resulting in a significant taste improvement, this method has been found not to completely eliminate the "throat burn" associated with ibuprofen in chewable dosage forms.

U.S. Pat. No. 4,762,702 discloses ibuprofen particles enveloped by a coating of hydrocolloid film, containing fumaric acid. The hydrocolloid performs the function of connecting the water insoluble ibuprofen particles to the sparingly soluble fumaric acid for use in a powder for reconstitution in liquid. The preferred hydrocolloid composition comprises xantham gum and/or maltodextrin. The amount of the fumaric acid is 10% of the amount of the ibuprofen, and from about 0.46% to about 0.64% of the total formula. The patent discloses this method as reducing the tendency of ibuprofen to irritate the esophagus and gastrointestinal tract.

Despite the disclosures of the above patents and application, a simpler and less costly method for providing a tastemasked ibuprofen composition with reduced throat burn is still desired.

SUMMARY OF THE INVENTION

The present invention provides racemic mixtures of propionic acid derivatives with fumaric acid in an amount from about 50 to about 150 percent of the amount of the propionic acid derivative. Typically the level of fumaric acid is from about 5% to about 60% by weight of the total dosage form. We have found that these relatively high levels of fumaric acid do not impart an unacceptably high sourness to the product, as would similar levels of other pharmaceutically acceptable acids. The present invention provides fumaric acid sufficient to reduce the burn sensation of propionic acid derivatives without the requirement of connecting the fumaric acid particles to the propionic acid derivative by incorporation in a hydrocolloid coating. Additionally, the present invention provides fumaric acid sufficient to reduce the burn sensation of propionic acid derivatives in compositions that are substantially free of a hydrocolloid agent. In a preferred embodiment the propionic acid derivative/fumaric composition is provided in a chewable form.

A method for inhibiting the burn sensation of racemic mixtures of propionic acid derivatives by providing an effective amount of fumaric acid is also provided.

DETAILED DESCRIPTION OF THE INVENTION

Propionic acid derivatives are a well known class of analgesic compounds. As used herein propionic acid derivatives are understood to include, but are not limited to, ibuprofen, naproxen, benoxaprofen, naproxen sodium, flurbiprofen, fenoprofen, fenbuprofen, ketoprofen, indoprofen, pirprofen, carpofen, oxaprofen, pranoprofen, microprofen, tioxaprofen, suprofen, alminoprofen, tiaprofenic acid, fluprofen and bucloxic acid. The structural formula is set forth in U.S. Pat. No. 4,923,898, hereby incorporated by reference. Propionic acid derivatives as defined herein are defined as pharmaceutically acceptable analgesics/non-steroidal anti-inflammatory drugs having a free $—CH(CH_3)COOH$ or $—CH_2CH_2COOH$ or a pharmaceutically acceptable salt group, such as $—CH(CH_3)COO—Na+$ or $CH_2CH_2COO—Na+$, which are typically attached directly or via a carbonyl functionality to an aromatic ring system.

Propionic acid derivatives are typically administered on a daily basis, with the daily dose ranging from about 50 to about 2000 milligrams, preferably from about 100 to 1600 and most preferably from about 200 to about 1200 milligrams.

Ibuprofen is a widely used, well known non-steroidal anti-inflammatory propionic acid derivative. Ibuprofen is chemically known as 2-(4-isobutylphenyl)-propionic acid. As used herein ibuprofen is understood to include 2-(4-isobutylphenyl)propionic acid as well as the pharmaceutically acceptable salts. Suitable ibuprofen salts include arginine, lysine, histidine, as well as other salts described in U.S. Pat. Nos. 4,279,926, 4,873,231, 5,424,075 and 5,510,385, the contents of which are incorporated by reference.

Fumaric acid is a widely available pharmaceutically acceptable acid. The concentration of fumaric acid present to inhibit the burn of propionic acid derivative will vary on the amount of burn reduction desired. Generally the level of fumaric acid is from about 50 to about 150 weight percent of the propionic acid derivative dosage. Typically the level of fumaric acid is from about 60 to about 100 percent by weight of the level of propionic acid derivative and most preferably from about 70 to about 90 percent by weight of the level of propionic acid derivative dosage. Typically the level of fumaric acid is from about 5% to about 60% by weight of the total dosage form. In a preferred embodiment, the fumaric acid is from about 7% to about 13% by weight of the final dosage form.

Fumaric acid has commonly been used as a pharmaceutical excipient, as have other pharmaceutically acceptable acids, such as citric, malic, and tartaric acids, generally at levels less than 1% by weight of the total formula. Most pharmaceutically acceptable acids are well known in the art to impart an objectionably high sour taste at levels in excess of 5 weight percent of the total formula.

Contrary to the teaching of prior disclosures, the present invention does not require the incorporation of a hydrocolloid material in contact with fumaric acid in the coating in order to be effective. Inclusion of hydrocolloid materials in the present invention is optional.

The present invention allows for a hydrocolloid to coat the racemic mixture of the propionic acid derivative, but if a hydrocolloid coating is provided on the propioinic acid derivative, no fumaric acid is to be incorporated in the hydrocolloid film. Instead, the fumaric acid is provided in the dosage form with the other excipients, such as flavors, sweeteners and the like.

In a preferred embodiment, the present invention is substantially free of hydrocolloids, that is understood to be less than about 7 weight percent of the final dosage form. In a highly preferred embodiment, the present invention contains a coating around the granulated racemic mixture of the propionic acid derivative which contains less than about 5 weight percent hydrocolloid, based on the total weight of the tablet, preferably less than about 4 weight percent and in some circumstances the coating does not contain any hydrocolloid.

Suitable hydrocolloid coatings include, but are not limited to, hydroxypropylcellulose, xantham gum, maltrodextrins, hydroxyethylcellulose, hydroxypropyl-methylcellulose, and mixtures of these materials.

The simplest preferred embodiment of the present invention is the incorporation of fumaric acid as an excipient, i.e., freely and randomly provided in a mixture. In this embodiment, the racemic mixture of the propionic acid derivative, preferably ibuprofen, and fumaric acid are provided in a mixture within the tablet, gel, semi-solid, liquid, or other desirable form.

In a particularly preferred embodiment of the present invention, the ibuprofen is granulated with other ingredients, and coated with polymers, as disclosed in U.S. Pat. No. 5,320,855 the contents hereby incorporated by reference as set forth here in its entirety. In this embodiment, the granulated and coated racemic mixture of the propionic acid derivative, preferably ibuprofen, and fumaric acid are provided in the tablet, gel, semi-solid, liquid, or other desirable form.

In another embodiment of the invention the ibuprofen and fumaric acid are provided in a granulation. Typically this involves the admixing of the propionic acid derivative, and fumaric acid as well as sugars, disintegrants, binders, water and other ingredients together using equipment well known in the art. For example, U.S. Pat. No. 5,215,755 discloses rotorgranulation methods, the contents hereby incorporated by reference as set forth here in its entirety. The granulated mixture is then dried, milled, and blended with additional excipients. The blended mixture is then in suitable form to be compressed into a tablet.

In a highly preferred embodiment the racemic mixture of propionic acid derivative/fumaric acid is provided such that a chewable tablet is available to those who have difficulty in swallowing a tablet.

The formulation of the present invention may also contain pharmaceutically acceptable excipients, fillers, flavors, diluents, lubricants, disintegration agents, suspension agents, stabilizer, binders, colorants, carriers and the like.

For example suitable carriers include lactose, starch, dicalcium phosphate, calcium sulfate, kaolin, mannitol and powdered sugar. Typical binders include starch gelatin, sugars (such as dextrose, mannitol, xylitol, sorbitol, maltodextrins, fructose, sucrose, molasses), and lactose, polyvinylpyrrolidone, polyethylene glycol, ethyl cellulose and waxes. Lubricants include boric acid, sodium benzoate, magnesium stearate, sodium acetate, sodium chloride, leucine, polyethylene glycol and the like. Typical disintegrants include, starch derived from wood, maize, potato, and rice, methylcellulose, magnesium silicates, aluminum silicates, sucrose, dextrose, maltodextrin, agar, alginic acid, wood products, guar gum, citric pulp, sodium lauryl sulfate and the like.

The present invention may be provided in liquid or semi-solid form, e.g. an elixir, suspension, syrup, gel, cream, ointment, or sugar cream confection such as a fondant or nougat. The liquid or semi-solid formulations are prepared using manufacturing methods and pharmaceutically acceptable surfactants, dispersants, sweeteners and diluents known in the art. Preferably the present invention is provided in tablets or other solid dosage forms and most preferably in a chewable form.

As used throughout this specification burn is understood to mean the commonly identified peppery or irritating sensation in the throat and/or mouth, noted when taking the racemic mixture of ibuprofen and related compounds. This burn is different than bitterness inasmuch as the addition of a sweetener is not effective in reducing the sensation.

Alternatively, the racemic mixture of ibuprofen and fumaric acid composition may be added at appropriate levels to beverages, food and other edible compositions which may be desired. It is also anticipated that the ibuprofen/fumaric acid compositions of the present invention may also be employed in veterinarian applications.

Without wishing to be bound by any theory the incorporation of fumaric acid to the propionic acid derivative reduces the characteristic burn by acidifying the saliva sufficiently to maintain the protonated form of the propionic acid derivative. The protonated form of the propionic acid derivative has low solubility and hence has low irritation to the throat mucosa. Unlike other acidulates, fumaric acid dissolves slowly such that its sour taste is minimal in the mouth but sufficient to acidify the throat. Other pharmaceutically acceptable acids, such as citric, malic, tartaric acids are much more soluble than fumaric acid. These and other acids impart an unacceptably high sour taste in the mouth very quickly. The dissolution is so rapid that an exclusive sour taste is perceived in the mouth well before the saliva in the throat is sufficiently acidified.

The invention will now be illustrated by, but is not intended to be limited to, the following examples. In these examples it is understood that unless noted otherwise, all parts are weight percent.

EXAMPLE 1

Chewable tablets containing 100 milligrams (mg) of active racemic mixture of ibuprofen, 76 weight percent ibuprofen granulated with polyvinyl pyrrolidone, sodium lauryl sulfate, sodium starch glycolate, and purified water, according to the method disclosed in U.S. Pat. No. 5,320,855 and coated with an 18 weight percent coating (131 total mg of ibuprofen, excipients and coating) comprised of hydroxyethylcellulose and hydroxypropyl methylcellulose, were prepared with either 70 mg of fumaric acid or with no fumaric acid. The chewable tablets which contain no fumaric acid were used as a control. A taste panel of eighteen subjects were asked to chew two control tablets and score the throat burn on a scale of 1 to 9 (highest level). After one hour, tablets containing the ibuprofen/fumaric acid combination were chewed and the subjects were again asked to score the results using the same 1–9 scale.

The subjects rated the control tablets as moderately high, as a 7 on a 9 point scale, whereas the tablets containing the ibuprofen/fumaric acid combination were rated as moderately low, a 3 or 4 on the 9 point scale.

EXAMPLE 2

The following formulation was found to be effective in eliminating the burn sensation. Coated racemic mixture of ibuprofen (131 grams total similar to that in Example 1), 100 milligrams (mg) active ibuprofen, coloring 1.76 mg; microcrystalline cellulose 84 mg; sweetener 11 mg; second sweetener 4 mg; flavoring 2 mg; lubricant 6 mg; excipient 465 mg; fumaric acid 65 mg.

EXAMPLE 3

Two subjects were used to determine the effective level of fumaric acid for a 100 mg dosage of coated ibuprofen. The subjects rated the ibuprofen/fumaric acid composition with the following scale. Burn intensity: extremely high 9; very high 8; moderately high 7; slightly high 6; neither high or low 5; slightly low 4; moderately low 3; very low 2; extremely low 1; no bitterness or burn 0. The average score of the test results are reported below:
30 mg fumaric acid 7
40 mg fumaric acid 6
50 mg fumaric acid 3
60 mg fumaric acid 1

This example demonstrates that 50 mg fumaric acid by weight per 100 mg of racemic mixture of active ibuprofen was effective in reducing the burn sensation of ibuprofen.

What is claimed is:

1. A method for reducing the burn sensation of propionic acid derivative compositions comprising:
   providing a therapeutically effective amount of a racemic mixture of a propionic acid derivative that is provided with a hydrocolloid coating, which is optionally provided as a granule containing active and excipients,
   providing from about 50 to about 150 weight percent of fumaric acid based upon the weight of propionic acid derivatives in an excipient formulation;
   admixing said racemic mixture of a propionic acid derivative and excipient formulation containing said fumaric acid to form a mixture;
   provided said coating is substantially free of fumaric acid.

2. The method of claim 1 wherein the racemic mixture of a propionic acid derivative is ibuprofen.

3. The method of claim 1 wherein the fumaric acid and racemic mixture of a propionic acid derivative are admixed in a granulation process.

4. The method of claim 1 wherein the granulation process is conducted with a non-hydrocolloid binder.

5. The method of claim 2 wherein the ibuprofen is granulated with excipients.

6. The method of claim 1 wherein the hydrocolloid coating consists essentially of one or more cellulose derivatives.

7. The method of claim 1 wherein the hydrocolloid is selected from the group consisting of hydroxyethylcellulose, hydroxypropyl methylcellulose, hydroxypropyl cellulose, hydroxymethylcellulose and mixtures thereof.

8. The method of claim 5 wherein the excipients are selected from the group consisting of polyvinylpyrrolidone, sodium starch glycolate and sodium lauryl sulfate, and cellulose derivatives.

\* \* \* \* \*